US010786372B2

(12) United States Patent
Yeh et al.

(10) Patent No.: US 10,786,372 B2
(45) Date of Patent: Sep. 29, 2020

(54) IMPLANTABLE VASCULAR DEVICE HAVING LONGITUDINAL STRUTS

(71) Applicant: Vascular Dynamics, Inc., Mountain View, CA (US)

(72) Inventors: Chung Hao Yeh, San Mateo, CA (US); Jennifer Gong, San Jose, CA (US); Brent Seybold, Santa Clara, CA (US); Christopher Ken, San Mateo, CA (US); Suji Shetty, San Jose, CA (US); Edward F. Ruppel, Jr., Saratoga, CA (US); Robert Stern, Los Altos, CA (US)

(73) Assignee: Vascular Dynamics, Inc., Mountain View, CA (US)

( * ) Notice: Subject to any disclaimer, the term of this patent is extended or adjusted under 35 U.S.C. 154(b) by 825 days.

(21) Appl. No.: 14/921,171

(22) Filed: Oct. 23, 2015

(65) Prior Publication Data

US 2016/0038317 A1    Feb. 11, 2016

Related U.S. Application Data

(63) Continuation of application No. PCT/US2014/035355, filed on Apr. 24, 2014.
(Continued)

(51) Int. Cl.
*A61F 2/86* (2013.01)
*A61F 2/915* (2013.01)
(Continued)

(52) U.S. Cl.
CPC ............... *A61F 2/86* (2013.01); *A61F 2/844* (2013.01); *A61F 2/91* (2013.01); *A61F 2/915* (2013.01);
(Continued)

(58) Field of Classification Search
CPC .... A61F 2/90; A61F 2/915; A61F 2/86; A61F 2/82; A61F 2230/0017; A61F 2230/0021
See application file for complete search history.

(56) References Cited

U.S. PATENT DOCUMENTS 6,129,755 A    10/2000 Mathis et al.
6,190,406 B1    2/2001 Duerig et al.
(Continued)

FOREIGN PATENT DOCUMENTS

JP    2008523846 A    7/2008
JP    2013506517 A    2/2013
WO    WO-03032871 A1 *    4/2003    ............... A61F 2/86

OTHER PUBLICATIONS

Co-pending U.S. Appl. No. 14/811,352, filed Jul. 28, 2015.
(Continued)

*Primary Examiner* — Brian E Pellegrino
(74) *Attorney, Agent, or Firm* — Wilson Sonsini Goodrich & Rosati

(57) ABSTRACT

An implantable frame comprises a plurality of corner structures configured to decrease pressure to the vessel wall and define pulsatility enhancing windows of the implantable frame. The corner structures may comprise plurality of neighboring longitudinal struts that extend in a longitudinal direction of the blood vessel when placed to form the vessel wall to a substantially polygonal cross-section and distribute pressure loading of the corner structure among the plurality of neighboring longitudinal struts to improve biocompatibility. The corner structures also allow increased forming of the vessel wall and can provide stretching of the vessel wall to enhance pulsatility of the vessel wall.

26 Claims, 10 Drawing Sheets

Related U.S. Application Data

(60) Provisional application No. 61/815,664, filed on Apr. 24, 2013.

(51) Int. Cl.
*A61F 2/844* (2013.01)
*A61F 2/91* (2013.01)

(52) U.S. Cl.
CPC .............. *A61F 2002/91558* (2013.01); *A61F 2230/0019* (2013.01); *A61F 2230/0021* (2013.01); *A61F 2240/008* (2013.01); *A61F 2250/0098* (2013.01)

(56) References Cited

U.S. PATENT DOCUMENTS

| | | |
|---|---|---|
| 8,923,972 B2 | 12/2014 | Gross |
| 9,125,567 B2 | 9/2015 | Gross et al. |
| 9,125,732 B2 | 9/2015 | Gross et al. |
| 2002/0123791 A1 | 9/2002 | Harrison |
| 2004/0254635 A1* | 12/2004 | Shanley ............... A61F 2/915 623/1.17 |
| 2007/0038291 A1 | 2/2007 | Case et al. |
| 2009/0248139 A1 | 10/2009 | Pellegrini |
| 2010/0030318 A1* | 2/2010 | Berra ..................... A61F 2/07 623/1.11 |
| 2011/0077729 A1 | 3/2011 | Gross et al. |
| 2011/0178416 A1 | 7/2011 | Gross et al. |
| 2011/0230953 A1 | 9/2011 | Gross |
| 2013/0172981 A1 | 7/2013 | Gross et al. |
| 2013/0304102 A1 | 11/2013 | Gross et al. |
| 2014/0135902 A1 | 5/2014 | Gross et al. |
| 2015/0119973 A1 | 4/2015 | Gross |

OTHER PUBLICATIONS

International search report and written opinion dated Sep. 29, 2014 for PCT/US2014/035355.

European Search Report dated Jan. 4, 2017 for European Patent Application No. EP1479866.2.

* cited by examiner

Diastolic to Systolic change of a normal vessel

— = Diastolic position of vessel (radius/diameter)
---- = Systolic position of vessel (radius/diameter)

Normal vessel change $\Delta_{norm} = 'd' - 'c'$ $$\boxed{\Delta_{norm}) = \frac{'d' - 'c'}{'c'}}$$

Vertical change = $\Delta_{vert} = \frac{'e' - 'a'}{2}$

Horizontal axis change = $\Delta_{hori} = \frac{'f' - 'b'}{2}$ $(\Delta_{vert}) = \frac{\Delta_{vert}}{'a'/2}$ $(\Delta_{hori}) = \frac{\Delta_{hori}}{'b'/2}$ $\boxed{\text{if } a < b, \text{ then } \Delta_{vert} > \Delta_{hori}}$ Normal vessel change

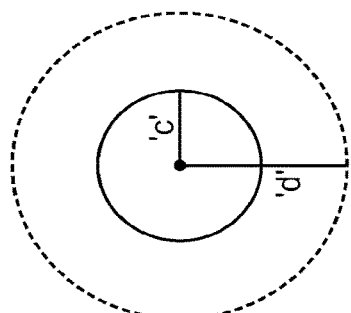

FIG. 6A

Reshaped vessel change

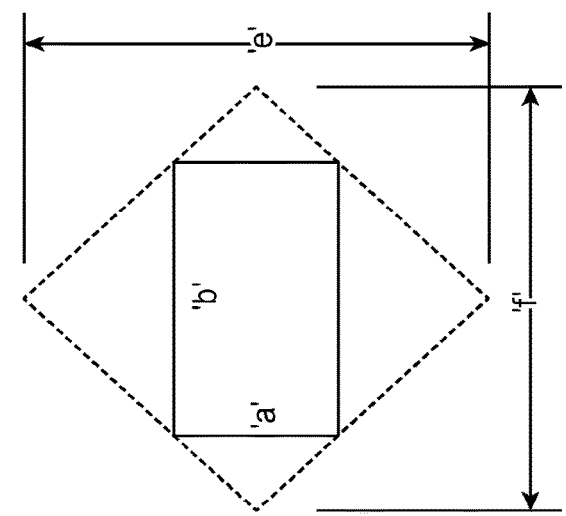

FIG. 6B

IMPLANTABLE VASCULAR DEVICE HAVING LONGITUDINAL STRUTS

CROSS-REFERENCE

The present application is a continuation of PCT App. No. PCT/US2014/035355, filed Apr. 24, 2014, entitled "IMPLANTABLE VASCULAR DEVICE HAVING LONGITUDINAL STRUTS"; which claims the benefit of U.S. Provisional App. No. 61/815,664, filed Apr. 24, 2013, the entire disclosure of which is incorporated herein by reference.

BACKGROUND

Field of the Invention

The present invention relates generally to medical apparatus and methods. More particularly, the present invention relates to apparatus and methods for shaping a portion of a blood vessel wall to enhance the response of a stretch receptor in a region of the wall.

Prior methods and apparatus of treating blood pressure provide less than ideal results in at least some instances.

Hypertension is a medical condition characterized by elevated blood pressure and can result from a number of underlying factors, including genetics, obesity, diet, and the like. When diagnosed, hypertension is most commonly treated by changes in diet, exercise, and pharmaceutical intervention. More recently, it has been proposed to treat hypertension and related conditions by stimulating or modulating certain receptors in the patient's vasculature, which may be referred to as stretch receptors, strain receptors or baroreceptors. Stretch receptors are located in the walls of blood vessels such as the carotid arteries and the aortic arch, and the like. It has been found that stimulating the baroreceptors and/or the nerves connected to the baroreceptors, can reduce a patient's blood pressure.

Mechanical stimulation of the baroreceptors within the internal carotid sinus may result in a drop of blood pressure. Baroreceptor nerves are stretch sensors surrounding the internal carotid artery, the aortic arch and other vasculature. An increase in blood pressure stretches the carotid sinus causing the baroreceptors to increase their basal rate of action generation. Action potentials are then conducted by the glossopharyngeal nerve to the central nervous system. This signaling modulates blood pressure. Research has suggested that stimulation of the baroreceptors in the vessel wall is helpful. If the pulsatile signal is lost, the baroreceptors reset and may no longer accurately sense blood pressure.

Though stents have been available for carotid placement for many years the major drawback is that they tend to have a detrimental impact on the pulsatility of the implanted vessels, and are less than ideally suited to reduce blood pressure.

In light of the above, it would be desirable to provide additional and alternative methods and apparatus for effecting or modulating baroreceptors and other stretch receptors in a clinically effective manner, particularly for the treatment of hypertension and related conditions. Also, it would be helpful to provide improved methods and apparatus that provide a greater baroreceptor stimulation and corresponding reduction in blood pressure than at least some of the prior methods and apparatus, while providing improved biocompatibility.

At least some of these objectives will be met by the inventions described herein.

SUMMARY

Embodiments of the present invention provide improved methods and apparatus of treating patients. The embodiments as described herein can be used to treat hypertension and one or more of many patient conditions associated with hypertension, such as heart conditions and renal conditions. In many embodiments, an implantable frame comprises a plurality of corner structures configured to decrease pressure to the vessel wall and define pulsatility enhancing windows of the implantable frame. The corner structures may comprise plurality of neighboring longitudinal struts that extend in a longitudinal direction of the blood vessel when placed to form the vessel wall to a substantially polygonal cross-section and distribute pressure loading of the corner structure among the plurality of neighboring longitudinal struts to improve biocompatibility. The corner structures also allow increased forming of the vessel wall and can provide increased force and shaping of the vessel wall to enhance pulsatility of the vessel wall.

In many embodiments, each of the corner structures comprise a plurality of openings defined with the neighboring longitudinal struts and a thickness dimensioned to promote growth of an endothelium of the blood vessel over the corner structures in order to enhance biocompatibility. The corner structures can be connected with a plurality of connecting members that retain the corner structures in a spaced apart arrangement to form the vessel wall and define a plurality of windows that enhance pulsatility of the vessel wall in order to lower blood pressure of the patient. The plurality of windows can be arranged rotationally around a longitudinal axis of the frame and may comprise from about three to about five windows. In many embodiments, the corner structures define a maximum transverse dimension across the frame and the corner structures receive a greater amount of force from the vessel wall than the connecting members when placed in the blood vessel in order to enhance pulsatility and lower blood pressure.

Additional aspects and embodiments of the invention are recited in the claims below, which are incorporated into the summary by reference.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 6A shows normal vessel shape change between a diastolic configuration and a systolic configuration, in accordance with embodiments;

FIG. 6B shows a formed ("reshaped" or "shaped") vessel change between a diastolic configuration and a systolic configuration with a frame dimensioned to amplify pulsation of the vessel wall, in accordance with embodiments;

DETAILED DESCRIPTION

Figure 1:
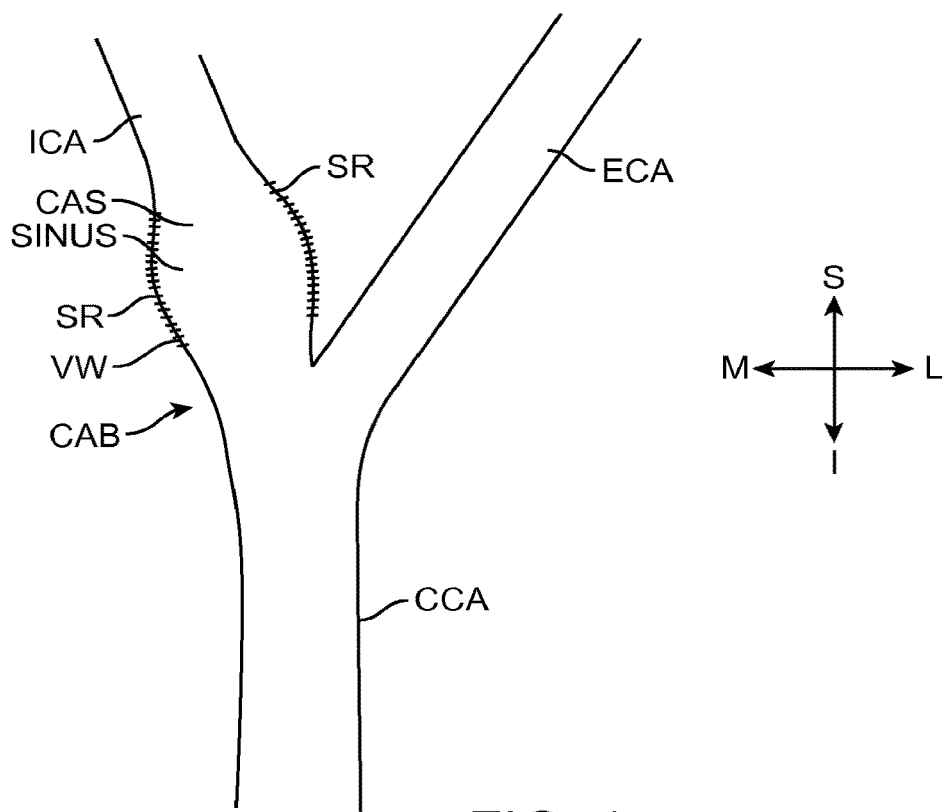
FIG. 1 shows the carotid artery comprising carotid sinus with stretch receptors, in accordance to embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure in accordance with embodiments. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

The implantable device as described herein can be used to treat hypertension, and the treatment of hypertension can improve heart function and renal function of the patient, for example. In some embodiments, the implantable device may delay or even avoid the onset of congestive heart failure and renal failure, for example.

The embodiments disclosed herein can be combined in one or more of many ways to provide improved implantable frames and methods.

As used herein like characters identify like elements.

Although specific reference is made to baroreceptors, the stimulated receptors may comprise stress or stretch receptors generally, and reference is made to baroreceptors by way of example in accordance with embodiments.

The implantable frame comprises a plurality a corner structures and connecting members coupled to the corner structures that define a plurality of pulsatility enhancing windows of the implantable device. While each of the corner structures can be formed in one or more of many ways, in many embodiments the corner structures comprise a plurality of neighboring longitudinal struts. Each of the plurality of neighboring longitudinal struts may comprise two or more neighboring longitudinal struts.

In many embodiments, the plurality of neighboring longitudinal struts provides a more uniform electro-polish, and distributes force against the wall of vessel in order to increase amplification of pulsatility of the vessel wall. The plurality of neighboring longitudinal struts of each corner structure can provide increased force and distribute the load on the vessel wall over an area while providing endothelial cell growth of the vessel wall over the implantable frame.

In many embodiments, the implantable frame provides a metal to artery ratio of no more than about 12%, for example no more than about 10.5% or no more than about 10%, when the frame is placed in an artery having a diameter of about 5 mm, for example. The metal to artery ratio may comprise a percentage of the surface area of the frame contacting the vessel wall divided by the surface area of the vessel wall that covers the windows and frame when placed. The surface area of the vessel wall that covers the frame can be determined by a longitudinal length of the frame and the surface area of the artery wall along the longitudinal length of the frame. The metal to artery ratio can depend on the size of the artery.

The implantable frame comprises corner structures having substantially straight struts oriented along the implant frame longitudinal axis and blood vessel longitudinal axis when placed. The straight length may comprise a substantial percentage of the implant frames overall length, for example greater than 30% in implants freely expanded unloaded configuration. In addition, this straight strut may have a substantial span between intersections with the connecting members forming a relatively long unsupported length, for example greater than 30% of the overall length of the device, in its freely expanded unloaded configuration. These embodiments can substantially decrease the number of strut-to-strut junctions formed with connecting members as well as the number of struts with curved geometry in the planar view, for example the laser path view.

The corner structures that increase the contact surface area allow the creation of large pulsatility enhancing windows, for example, with structures that reduce the contact pressure against the vascular wall. These structures distribute the loads to prevent vascular damage and allow endothielization. These structures may include the "doubling-up" of neighboring longitudinal struts connected with transverse members so that two or more neighboring struts may take the place of a single strut in the corner structure.

In many embodiments, the pulsatility enhancing windows are sized to inhibit endothelial hyperplasia near the central portion of the window away from the corner structures and connecting members, for example, in order to promote pulsatility of the vessel wall.

Although the pulsatility enhancing windows as described herein may comprise cells in accordance with some embodiments, the pulsatility enhancing windows as described herein differ substantially from the cells of prior stents, as the cells of prior stents inhibit pulsatility of the vessel wall.

The implantable frame may have a plurality of peripheral windows arranged in a row around the periphery of the frame about the longitudinal axis. In many embodiments a single peripheral row of windows is provided around the periphery of the device about the longitudinal axis.

In many embodiments, a window comprises an opening between corner structures, and the window is defined with two corner structures and the two corresponding connecting members that connect and support the corner structures. Each window spans the majority of the overall longitudinal length of the frame, for example the window length can be at least about 60% of overall length of expanded frame.

Embodiments provide a frame with a low metal to artery ratio of the contact surface profile that engages the arterial wall, for example no more than 10% and an appropriate number of pulsatile windows in order to provide enhanced pulsatility. In many embodiments, the frame comprises 3, 4 or 5 windows to provide enhanced pulsatility. Work in relation to embodiments suggests that as the number of pulsatile windows increases, the area of the vessel wall shaped with the windows decreases. The windows can be arranged in a side by side configuration in order to form the pulsatility enhancing windows inside the lumen. The cross-sectional shape of the vessel wall may be determined by the number of windows. A frame having a single window may form a plane, and a frame having two windows may form a rectangular cross-section with a high aspect ratio, and a frame with 3 windows a triangle, 4 windows a quadrilateral, 5 windows a pentagon, and 6 windows a hexagon, for example. A single window may create two large flat sections of the arterial wall, while 3 windows would can create 3 flat sections of the arterial, wall, for example. The windows provide large flattened areas with of the vessel wall with a substantially reduced radius of curvature while inhibiting effects on blood flow and decreasing exposure of the frame to the vasculature, for example by providing growth of the endothelium over the implantable frame.

Figure 2:
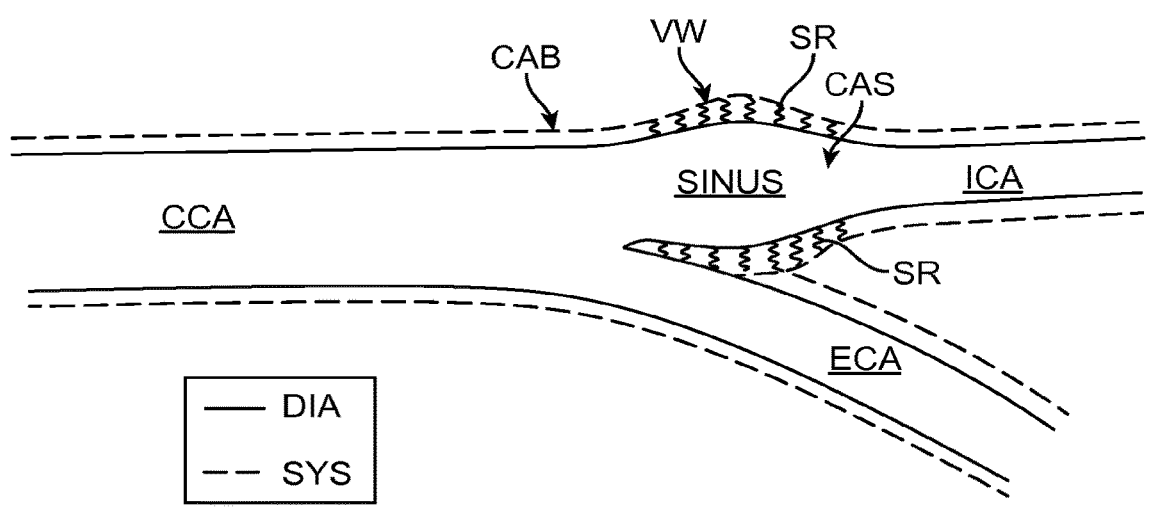
FIG. 2 shows the carotid artery as in FIG. 1 during diastole and systole, in accordance to embodiments.

FIGS. 1 and 2 show a blood vessel suitable for incorporation in accordance with embodiments. FIGS. 1 and 2 are external and cross-sectional views, respectively, of the blood vessel. The blood vessel may comprise an artery for example. The vessel may comprise an artery such as the carotid artery or the aortic arch. The carotid artery comprises a carotid sinus CAS. The carotid artery comprises a common carotid artery CCA and the bifurcation CAB, where the common carotid artery CCA bifurcates into the internal carotid artery ICA and the external carotid artery ECA. The carotid sinus CAS comprises baroreceptors also referred to herein as stretch receptors SR. The stretch receptors SR are located in the vascular wall VW. The carotid sinus comprises many stretch receptors, that may be located distal to the bifurcation CAB. The stretch receptors may be unevenly distributed around the circumference of the blood vessel for a given longitudinal location along the axis of the artery, for example.

The patient anatomy may comprise a superior direction S, an inferior direction I, a medial direction M, and a lateral direction L, as will be understood by a person of ordinary skill in the art. Stimulation of the stretch sensors or baroreceptors within the internal carotid sinus results in a drop of blood pressure. Baroreceptor nerves are stretch sensors surrounding the internal carotid artery. An increase in blood pressure stretches the carotid sinus causing the baroreceptors to increase their basal rate of action generation. Action potentials are then conducted by the glossopharyngeal nerve to the central nervous system. This signaling modulates blood pressure. In order for the baroreceptor nerves to control blood pressure, vessel pulsatility is helpful. If the pulsatile signal is lost, the baroreceptors may reset and no longer accurately sense blood pressure.

Embodiments are configured to maintain pulsatility of the vessel wall and to amplify the signal seen by the baroreceptors. By reshaping the artery to provide a cross-section having three or more substantially flattened sides, the implantable frame increases the rate of change and amplitude of the vessel wall movement. This leads to higher and more frequent afferent signaling from the baroreceptors to the central nervous system that lower blood pressure of the patient.

A circular vessel allows the strain/displacement to be uniformly distributed around the circumference of the carotid sinus. However, by changing the form of the sinus to one that has substantially flattened sides shaped with the windows, the displacement of the vessel wall in the flattened portions over these windows is amplified with concomitant pulsatile flow. For example, an implantable device with four windows defined with four corner structures and eight connecting members may provide a vessel wall having four sides and a rectangular cross-section. Other examples include an implantable device three windows defined with three corner structures and six connecting members which may provide a vessel wall having three sides and a triangular cross-section and an implantable device three windows defined with five corner structures and ten connecting members which may provide a vessel wall having five sides and a pentagon cross-section. This amplification leads to a larger peak-to-peak difference in strain/displacement as compared to the strain experienced by the uniform diameter change with a circularly-shaped vessel. In vitro testing of the current embodiment demonstrates the ability of the device to increase the peak-to-peak amplitude of movement by more than 2× in a mock vessel when compared to a non-implanted section of the same vessel.

Figures 3A, 3B:
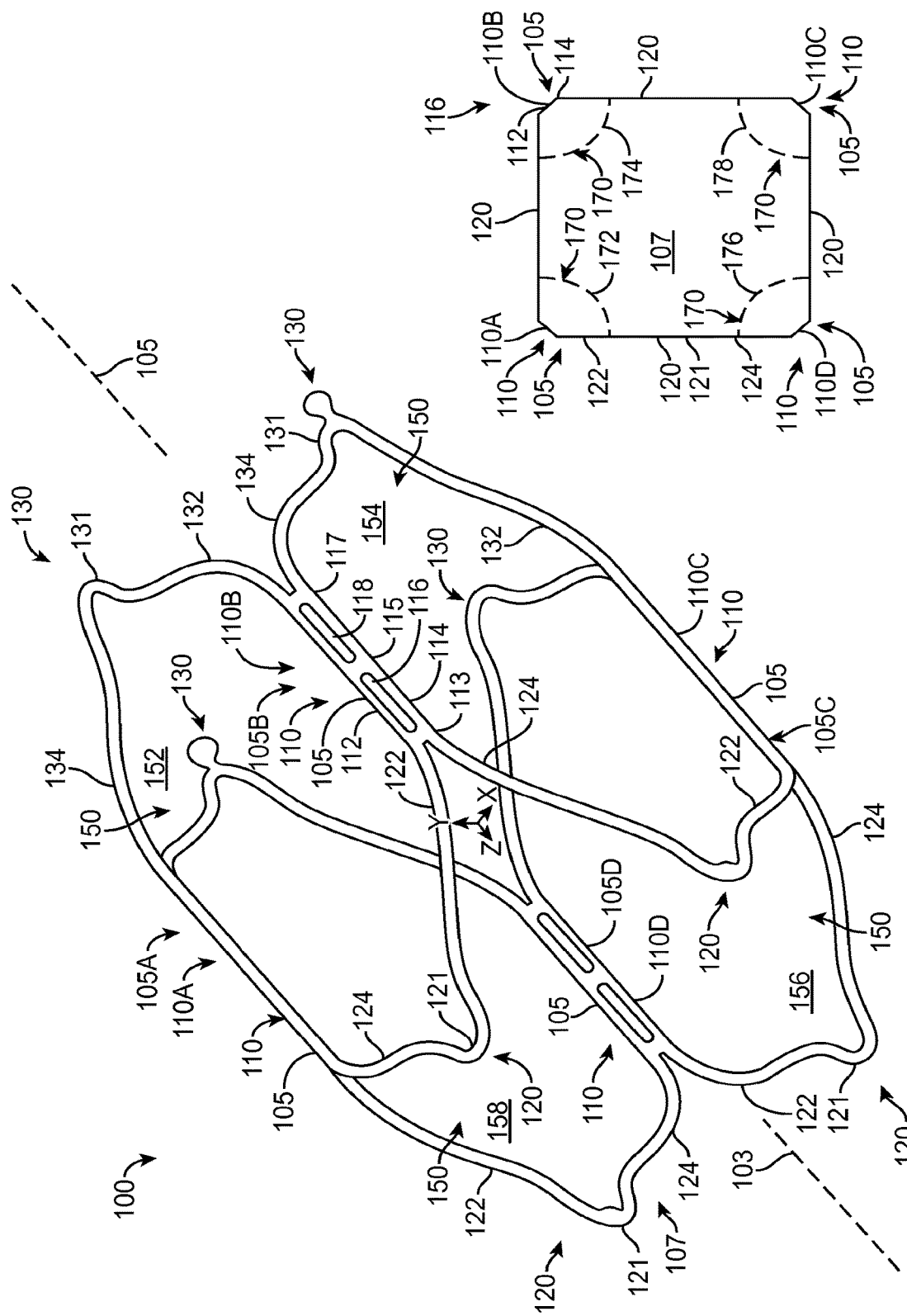
FIG. 3A shows an implantable frame in an expanded configuration for deployment, in accordance with embodiments.
FIG. 3B shows an end view of the implantable frame of FIG. 3A in the expanded configuration, in accordance with embodiments.

As shown in FIG. 2, during systole SYS the carotid artery expands and comprises an expanded configuration as shown by the dash line. During diastole DIA the carotid artery comprises a decreased size as shown by the solid line. The change in size stretches the vessel wall and stimulates the stretch receptors. Although the carotid artery is shown, the stimulated stretch receptors combined with the methods and apparatus as described herein may comprise stretch receptors at other locations of the vasculature such as the aortic arch, renal arteries, subclavien artery, braciocephalic artery, and the like The embodiments as described herein can provide an amplification of the baroreceptor response curve so as to lower the patient's blood pressure and allow the patient to increase or decrease blood pressure in response to environmental stimulus such as exercise, as appropriate. The embodiments as described herein can provide an improved sensitivity of the baroreceptor response curve, such that the patient can have lowered blood pressure and while retaining a natural response to stress and provide appropriate response to increased activity and decreased activity FIG. 3A shows an implantable frame 100 in an expanded configuration for deployment, in accordance with embodiments. The expandable frame 100 is configured to form the arterial wall to enhance pulsatility of the vessel wall and decrease blood pressure. The expandable frame 100 comprises a longitudinal axis 103 that is substantially aligned with a longitudinal axis of the artery when placed. In the expanded configuration, the expandable frame 100 defines an opening 107 through which blood can flow and pulsate the arterial wall. The expandable frame 100 comprises a plurality of windows 150 shaped to allow the vessel wall to pulsate. The plurality of windows may comprise a first window 152, a second window 154, a third window 156, and a fourth window 158. Each of the windows is shaped to form the vessel wall to increase deflection of the vessel wall.

The expandable frame 100 comprises a plurality of corner structures 105, a first plurality of connecting members 120 on a first end and a second plurality of connecting members 130 on a second end. The plurality of corner structures 105 may comprise a first corner structure 105A, a second corner structure 105B, a third corner structure 105C and a fourth corner structure 105D, for example when the vessel wall cross-section is formed to a substantially a quadrilateral cross-section. Each of the plurality of corner structures 105 comprises a plurality of neighboring struts 110. The plurality of neighboring struts may comprise a first plurality of neighboring struts 110A, a second plurality of neighboring struts 110B, a third plurality of neighboring struts 110C, and a fourth plurality of neighboring struts 110D, for example. Each of the plurality of corner structures may have a corresponding plurality of neighboring struts, for example first corner structure 105A, second corner structure 105B, third corner structure 105C and fourth corner structure 105D may individually correspond to first plurality of neighboring struts 110A, second plurality of neighboring struts 110B, third plurality of neighboring struts 110C and fourth plurality of neighboring struts 110D, respectively.

The plurality of neighboring struts of each of the corner structures 105 and the connecting members 120 and connecting members 130 define a plurality of windows 150. Each of the plurality of windows 150 is shaped to form the tissue to increase pulsatility of the vessel wall. In many embodiments, the vessel wall is shaped to a substantially polygonal cross-section in order to enhance pulsatility of the vessel wall.

Each of the plurality of corner structures 105 is configured to distribute pressure to the vessel wall and allow the endothelium of the vessel wall to grow over the corner structure 105 in order to increase biocompatibility. Each corner structure 105 comprises the plurality of neighboring struts 110 joined with connecting members that define openings of the corner structure that allow endothelium of the vessel wall to grow over the corner structure. The corner structure 105 comprises a first strut 112 and a second strut 114. The first strut 112 and the second strut 114 are joined with a plurality of transverse members comprising first transverse member 113, second transverse member 115, and third transverse member 117, for example. The plurality of struts and transverse members define a first opening 116 comprising a first slot and a second opening 118 comprising a second slot.

The first plurality of connecting members 120 and the second plurality of connecting members 130 can be configured in one or more of many ways. Each of the first plurality of connecting members 120 may comprise a first extension 122, a second extension 124 and an intermediate portion 121. The first extension 122 extends to first strut 112. The second extension 124 extends to second strut 114. Each of the second plurality of connecting members 130 may comprise a first extension 132, a second extension 134 and an intermediate portion 131. The first extension 132 extends to first strut 112. The second extension 134 extends to second strut 114.

When the implantable frame 100 expands from the first narrow profile configuration to the second expanded profile configuration, each of the plurality of connecting members is expanded while the corner structures comprising the plurality of longitudinal struts and connecting members remain in a substantially fixed arrangement. The first extension and the second extension of each of the connecting members can be urged apart so as to define the plurality of windows while the plurality of neighboring longitudinal struts and connecting members remain substantially undeflected. In alternate embodiments, the transverse members may deflect when the connecting members expand.

The plurality of windows 150 extend around an outer boundary of the frame 100 in order to shape the vessel wall and define the substantially polygonal cross-section with the plurality of corner structures 105. The substantially polygonal cross section may comprise a triangular cross-section, a quadrilateral cross-section, or a pentagonal cross-section, for example. As the blood vessel wall comprises a substantially polygonal cross-section, the wall of the blood vessel shaped with the connecting members will be shaped so as to deflect inwardly and outwardly when the connecting members and struts are fixed to the vessel wall, such that the substantially polygonal cross-section may comprise convex and concave portions extending between the corner structures when engaged with the frame, for example.

The shape of each of the plurality of windows 150 can be defined with the plurality of corner structures 105 and the first plurality of connecting members 120 on a first end of frame 100 and a second plurality of connecting members 130 on a second end of frame 130 opposite the first end.

Each of the plurality of struts can be configured in one or more of many ways to distribute the pressure of the corner structure comprising the plurality of struts. Each of the plurality of neighboring struts 110 may comprise from about two to about five neighboring struts for each corner structure 105, for example. Each of the plurality of longitudinal struts can be connected with a two or more transverse members, for example three or more transverse members. The number of openings defined with each of plurality of struts can be within a range from about 1 to 100 for example.

FIG. 3B shows an end view of the implantable frame 100 of FIG. 3A in the expanded configuration, in accordance with embodiments. The corner structures 105 are joined with the plurality of connecting members 120 on the first end and with the second plurality of connecting members on the second end. Each of the corner structures 105 is oriented with respect to the connecting members so as to define a plurality of angles 170 of the connecting members. The plurality of angles comprises a first angle 172, a second angle 174, a third angle 176 and a fourth angle 178, defined with first plurality of neighboring struts 105A, second plurality of neighboring struts 105B, third plurality of neighboring struts 105C, and fourth plurality of neighboring struts 105D, respectively. The angles can be similar or different, and may correspond to angles of a triangle, a quadrilateral, or a pentagon, for example.

Figure 3C:
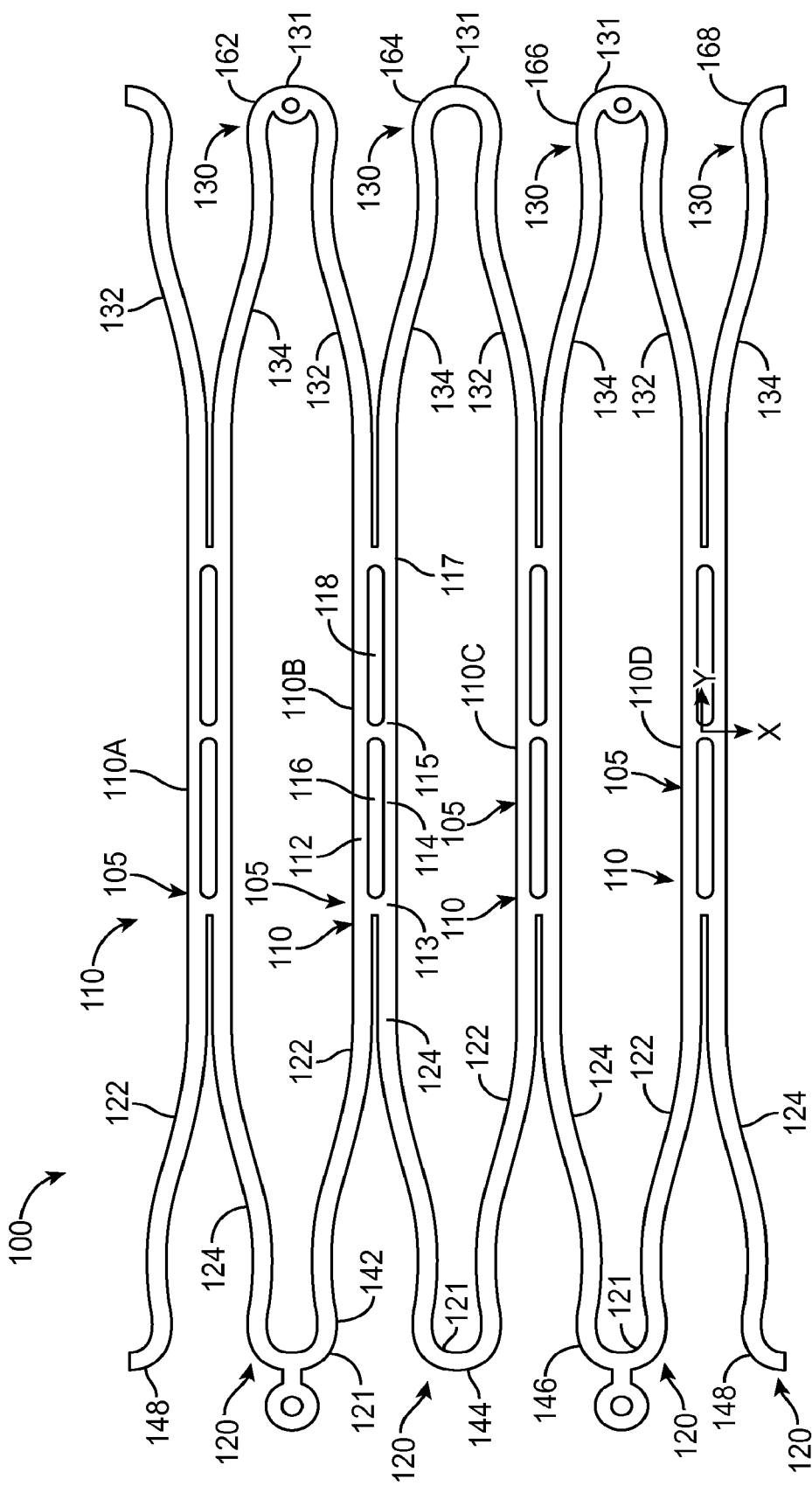
FIG. 3C shows a flat pattern view of the implantable frame of FIGS. 3A and 3B, in accordance with embodiments.

FIG. 3C shows a flat pattern view of the implantable frame of FIGS. 3A and 3B, in accordance with embodiments. The implantable frame can be rolled to a form a narrow profile configuration of the frame 100 for delivery to a target site such as the carotid artery. The first plurality of connecting members 120 comprises a first connecting member 142, a second connecting member 144, a third connecting member 146 and a fourth connecting member 148. The second plurality of connecting members 130 comprises a first connecting member 162, a second connecting member 164, a third connecting member 166 and a fourth connecting member 168.

When placed the target site such as the carotid sinus, the implantable frame can expand from the narrow profile configuration to the wide profile configuration with expansion of the connecting members such as first connecting members 120 and second connecting members 130 as described herein.

In many embodiments, the transverse members connect to the neighboring longitudinal struts on the ends of the struts between the struts and the connecting members in order to inhibit separation and deflection of the neighboring longitudinal struts. The transverse members can be located on the ends of the neighboring longitudinal struts between the struts and connecting members. For example, transverse member 113 and transverse member 117 are located on the ends of neighboring struts 112 and 114 to inhibit separation of the second plurality of struts 110B. The other pluralities of neighboring longitudinal struts can be similarly connected to the transverse members as described herein.

Additional structures can be provided on the implantable frame, such as radio opaque markers and openings for handling the frame with a tool, and these structures can be provided on the connecting members, for example.

Figure 4:
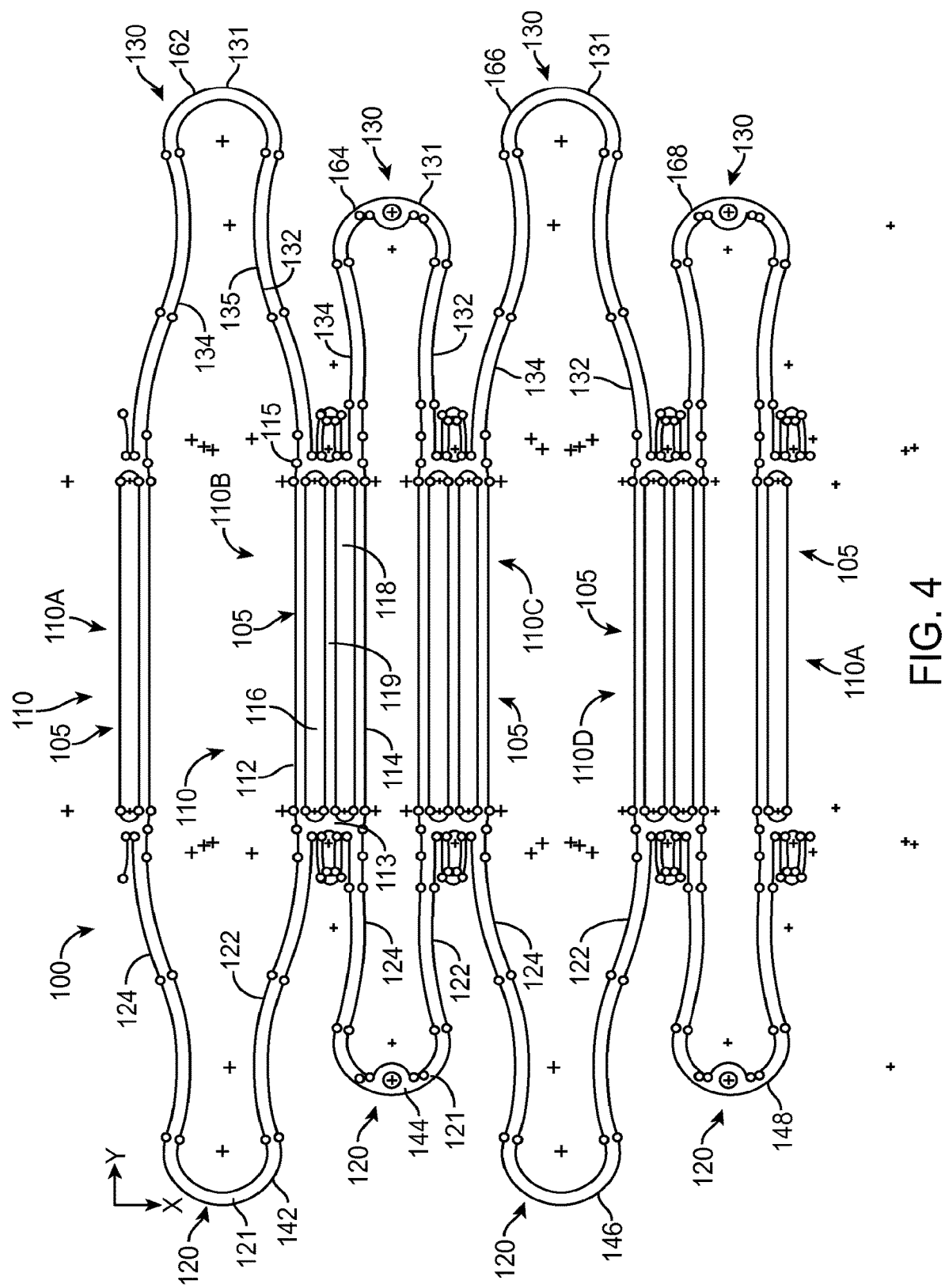
FIG. 4 shows a pattern view of an implantable frame having corner structures comprising a plurality of openings and neighboring longitudinal struts, in which a plurality of substantially parallel slots extend between the plurality of neighboring struts of each corner structure, in accordance with embodiments.

FIG. 4 shows a pattern view of an implantable frame comprising a plurality of openings and struts, in which a plurality of substantially parallel slots extend between each of the plurality of neighboring struts, in accordance with embodiments. Each of the plurality of neighboring longitudinal struts 110 comprises first longitudinal strut 112, second longitudinal strut 114 and a third longitudinal strut 119. The third longitudinal strut 119 is located between the first longitudinal strut 112 and the second longitudinal strut 114 to define a plurality of openings comprising first slot 116 and second slot 118. The plurality of transverse members comprises first transverse member 113 and second transverse member 115 located on opposite ends of the struts in order to define the ends of the slots. The plurality of transverse members may extend to the ends of the plurality of neighboring longitudinal struts to define the ends of the slots.

In many embodiments, the transverse members connect to the neighboring longitudinal struts on the ends of the struts in order to inhibit separation and deflection of the neighboring longitudinal struts. The transverse members can be located on the ends of the neighboring longitudinal struts between the longitudinal struts and connecting members. For example, transverse member 113 and transverse member 115 are located on the ends of neighboring struts 112, 114 and 119 to inhibit separation of the second plurality of struts 110B. The other pluralities of neighboring longitudinal struts can be similarly connected to the transverse members as described herein.

Figure 5B:
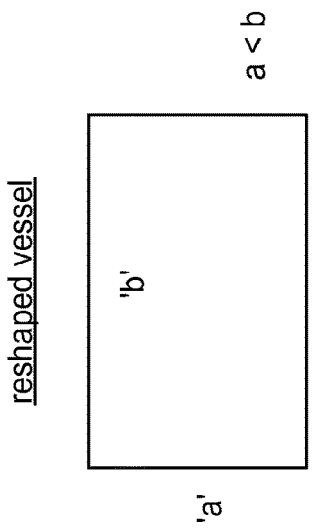
FIG. 5B illustrates a cross-section of the formed vessel wall of FIG. 5A.
Figure 5D:
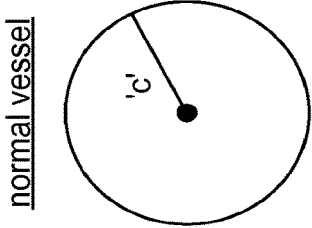
FIG. 5D illustrates a cross-section of the normal vessel wall of FIG. 5C.
Figure 5A:
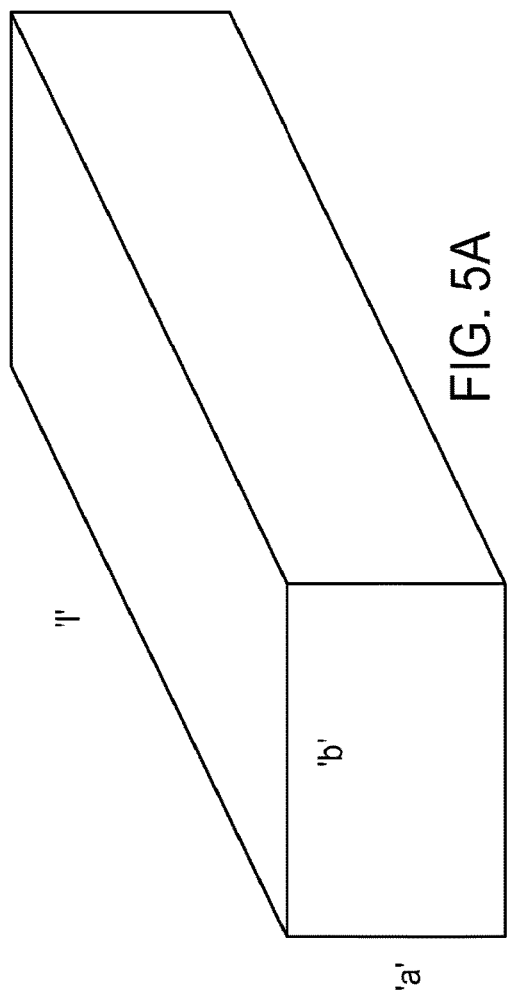
FIG. 5A illustrates a formed ("shaped") vessel wall during diastole, in accordance with embodiments.

FIG. 5A illustrates a formed ("shaped") vessel wall during diastole, in accordance with embodiments. The shaped vessel wall may comprise a block shaped geometry, for example.

FIG. 5B illustrates a cross-section of the formed vessel wall of FIG. 5A. The vessel wall may comprise four sides so as to define a rectangular shape, for example. The dimensions of the cross-section may comprise a first dimension A and a second dimension B of a quadrilateral for example. The first dimension A and the second dimension B can be different so as to define a rectangular cross-section. The first dimension A and the second dimension B can be substantially the same so as to define a square cross-section. The polygonal cross-section of the shaped vessel wall may comprise a number of sides within a range from about two to six, for example within a range from three to five sides. A person of ordinary skill in the art will recognize many variations and can appropriately modify the equations based on the teaching provided herein.

Figure 5C:
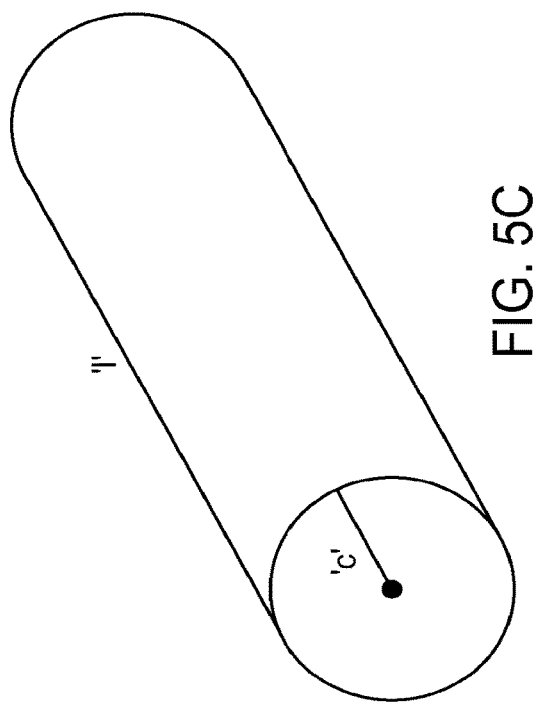
FIG. 5C illustrates a normal vessel wall during diastole, in accordance with embodiments.

FIG. 5C illustrates a normal vessel wall during diastole, in accordance with embodiments. The vessel wall may comprise a cylindrical geometry for example, approximating the shape of the sinus of the carotid artery, for example.

The changes can be expressed as a percentage (%)

FIG. 5D illustrates a cross-section of the normal vessel wall of FIG. 5C.

FIG. 6A shows normal vessel shape change between a diastolic configuration and a systolic configuration, in accordance with embodiments. The vessel wall comprises a diastolic diameter C and a systolic diameter D. The normal vessel change (Delta) can be defined as:

Delta (normal)=D−C. The normal vessel change can be expressed as a percentage ratio or fraction, such as:

$$\% \text{ Delta}=((D-C)/C)*100$$

FIG. 6B shows a formed ("reshaped" or "shaped") vessel change between a diastolic configuration and a systolic configuration, in accordance with embodiments. The diastolic dimensions may comprise A and B. The systolic dimensions may comprise E and F, in which dimension A corresponds to dimension E and dimension B corresponds to dimension F. The vertical change can be defined as:

$$\text{Delta Vert}=(E-A)/2.$$

The horizontal change can be defined as $$\text{Delta Horiz}=(F-B)/2.$$

The changes can be expressed as fractions such as percentages, for example as:

$$\% \text{ Vert}=(\text{Delta Vert})/(A/2); \text{ and}$$

$$\% \text{ Horiz}=(\text{Delta Horiz})/(B/2).$$

If A is greater than B then Delta Vertical is greater than Delta Horizontal.

A person of ordinary skill in the art will recognize that vertical and horizontal are provided as illustrative references by way of convenience and refer to a first cross-sectional dimension of the wall and a second cross-sectional dimension of the wall, which can be orthogonal to each other, for example.

Figure 6C:
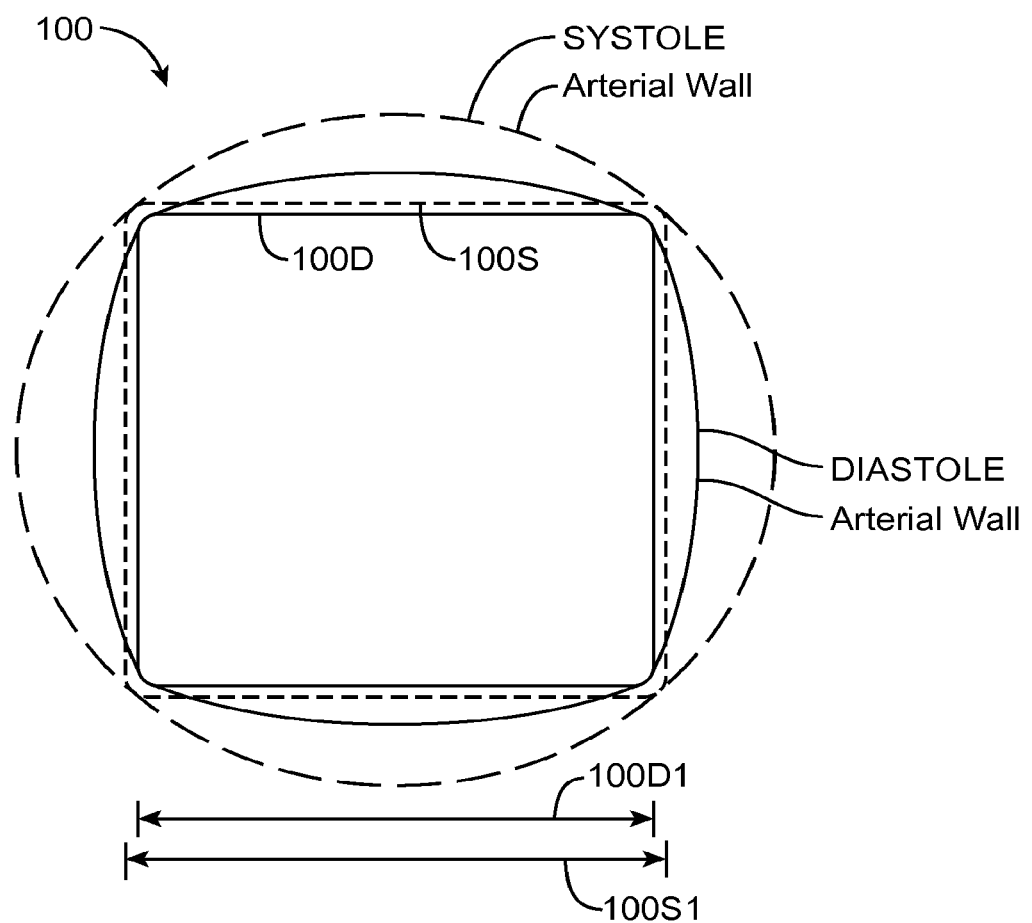
FIG. 6C shows a cross-sectional view of a vessel with an implanted device and vessel shaping during systole and diastole, in accordance with embodiments.

FIG. 6C shows a cross-sectional view of a vessel with an implanted device 100 as described herein and vessel shaping during systole and diastole. The frame 100 is shown in a diastolic configuration 100D and a systolic configuration 100S. The diastolic configuration 100D comprises a cross-sectional dimension 100D1 as described herein. The systolic configuration 100S comprises a cross-sectional dimension 100S1 as described herein. The diastolic cross-sectional dimension 100D1 is less than the systolic cross-sectional dimension 100S1. The systolic cross-sectional dimension 100S1 and the diastolic cross-sectional dimension 100D1 may each comprise a maximum cross-sectional dimension, for example a diagonal distance between corners of the cross-section as shown. The change in the cross-sectional dimension with systole and diastole may comprise a percent change as described herein.

A person of ordinary skill in the art would understand that FIG. 6B shows dimensions and that the vessel wall would be round as shown in 6C.

In many embodiments, by reshaping the artery to a non-circular cross-section the implantable frame device increases the rate of change and amplitude of the vessel movement. This increase in the rate of change and amplitude of the vessel movement provides higher and more frequent afferent signaling to the central nervous system from the baroreceptors as described herein. In many embodiments, the arterial wall cross-section comprises a substantially circular cross-section during systole in order to increase stimulation of stretch receptors, for example maximize stimulation of stretch receptors.

The mechanism of action can be described at least in part with the hoop stress equation, in many embodiments. The hoop stress shows that by changing the vessel to have flatter sections having decreased curvature under diastole, the radius of curvature is increased substantially, for example at least about 2× the diastolic curvature of the blood vessel without the implantable frame 100. For example, in many embodiments the diastolic radius of curvature of the vessel wall increases by at least about 4×, such as at least about 10×. This increased radius of curvature increases the differential strain (or Stress) seen by the baroreceptors.

The Hoop Stress equation can be expressed as follows:
Rdiastole=Approximates an infinite radius of curvature,
Rsystole=normal vessel wall radius of curvature under systolic pressure $$\varepsilon = \frac{pr}{tE}$$

ε=strain
p=pressure inside artery
r=artery internal radius
t=artery wall thickness
E=Young's Modulus Based on the above equation, a person of ordinary skill in the art can determine the strain of the vessel wall strain in accordance with embodiments as disclosed herein.

Figure 7:
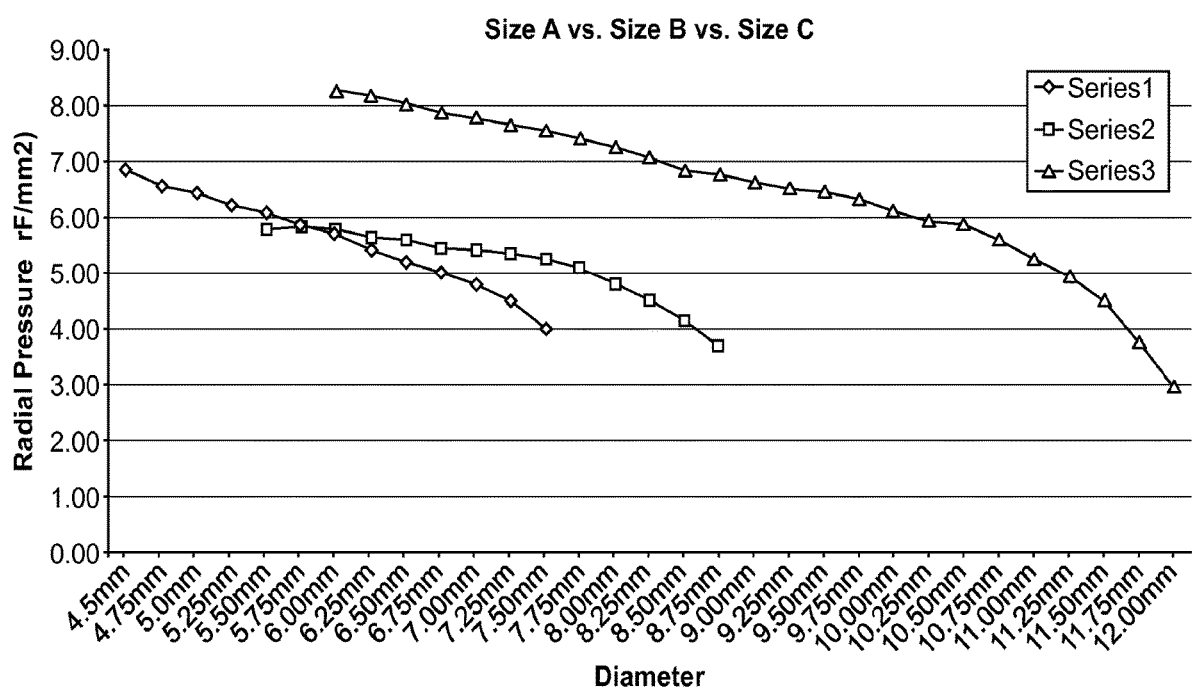
FIG. 7 shows radial pressure and diameter based on belt loop testing to determine forces an upper threshold and a lower threshold, in accordance with embodiments.

FIG. 7 shows radial pressure (grams-Force per mm$^2$, hereinafter "gF/mm2") and diameter based on belt loop testing to determine forces an upper threshold and a lower threshold, in accordance with embodiments. The belt loop testing can be performed with a belt loop testing apparatus similar to apparatus known and used to test stents.

The belt loop testing apparatus generally comprises a pair of rollers and thin film such polyethylene terephthalate (hereinafter "PET") commercially available as Mylar™. A belt of the film extends through the rollers defines a loop in which the test frame is placed.

The belt loop testing provides a belt having a circumference corresponding to a diameter of the tested frame. As used with the belt loop testing described herein, the diameter corresponds to a maximum dimension across the implantable frame as defined with the corner structures as described herein.

Similar testing can be conducted with commercially available devices such as a Blockwise radial force tester available from Blockwise Engineering.

The testing was conducted to determine radial force, and the radial force per unit area was determined based on the radial force and vessel contact area of the frame in order to determine the radial contact pressure (gF/mm2) of the device. The Radial Diameter of the belt loop corresponds to the maximum dimension across a cross-section of the implantable frame in accordance with embodiments described herein. The radial diameter corresponds to a maximum dimension across the device 100 defined with the plurality of corner structures as described herein. The radial pressure and radial diameter were determined for three sizes of devices, Size A, Size B and Size C, in accordance with embodiments described herein. Size A corresponds to a diameter of a vessel wall within a range from about 5 mm to about 7 mm; size B corresponds to a vessel wall having a diameter within a range from about 6 to about 9 mm; and size C corresponds to a vessel wall having a diameter within a range from about 8 to 12 mm, for example. The diameter corresponds approximately to the maximum dimension across a cross section of the device, and the Radial Pressure corresponds to a pressure of the vessel wall.

A person of ordinary skill in the art can determine force per unit area based on conversion of grams force to Newtons ("N") based on the teachings described herein.

TABLE 1

Testing results.

| | Vessel Range | Blockwise Method | | Belt Loop Method | |
| --- | --- | --- | --- | --- | --- |
| | | UTL | LTL | UTL | LTL |
| Frame A | 5-7 mm | 70 gF/mm2 | .35 gF/mm2 | 20 gF/mm2 | .1 gF/mm2 |
| Frame B | 6-9 mm | 70 gF/mm2 | .35 gF/mm2 | 20 gF/mm2 | .1 gF/mm2 |
| Frame C | 8-12 mm | 70 gF/mm2 | .35 gF/mm2 | 20 gF/mm2 | .1 gF/mm2 |

The belt loop testing shows that an upper threshold (hereinafter "UTL") can be about 20 gF/mm2, for example about 12 gF/mm2, and a lower threshold (hereinafter "LTL") can be about 0.1 gF/mm2, for example about 0.5 gF/mm2. The device can provide deflection within these ranges, for example. The range of radial pressure can be within a range from about 0.1 gF/mm2 to about 20 gF/mm2, for example. The radial pressure can be determined based on the radial force of the frame against the belt and the contact area of the frame against the belt. The contact area of the frame can be determined based on the surface area of the frame in the pattern view as disclosed herein, for example.

The belt loop testing results can be used to determine values that can be obtained with the Blockwise testing method. The belt loop testing results can be scaled to the estimated Blockwise values with a scale conversion of about 3.5× based on some of the test samples. Although the conversion can be a bit non-linear the 3.5× scaling can be used to determine the ranges and construct implantable frames based on the teachings provided herein.

Figure 8:
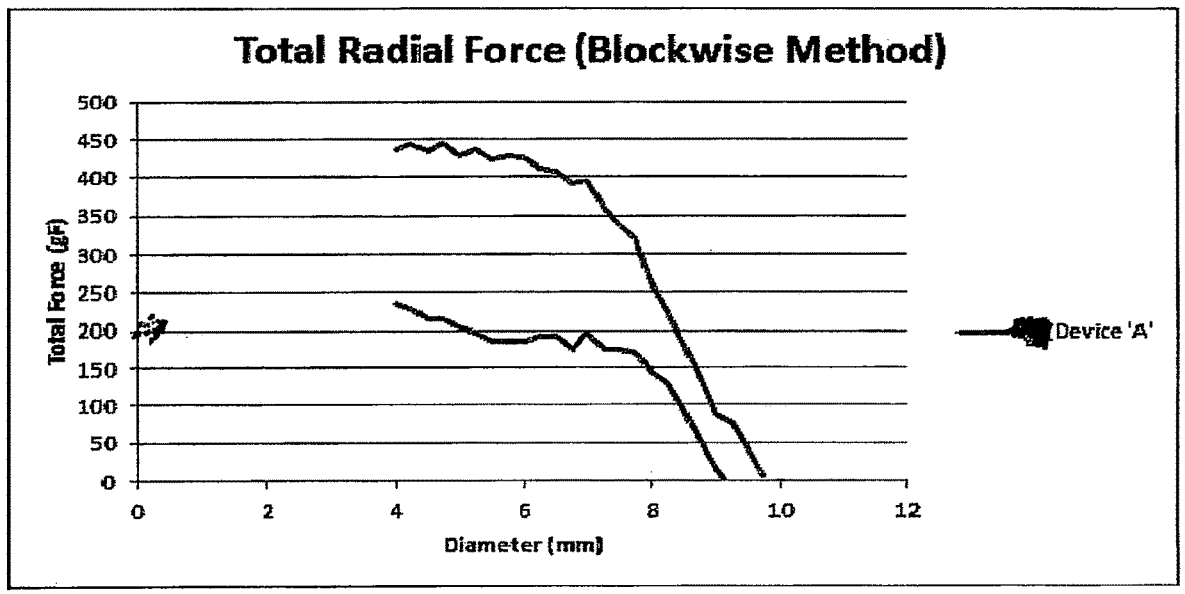
FIG. 8 shows total radial force versus diameter for a device in accordance with embodiments.
Figure 9:
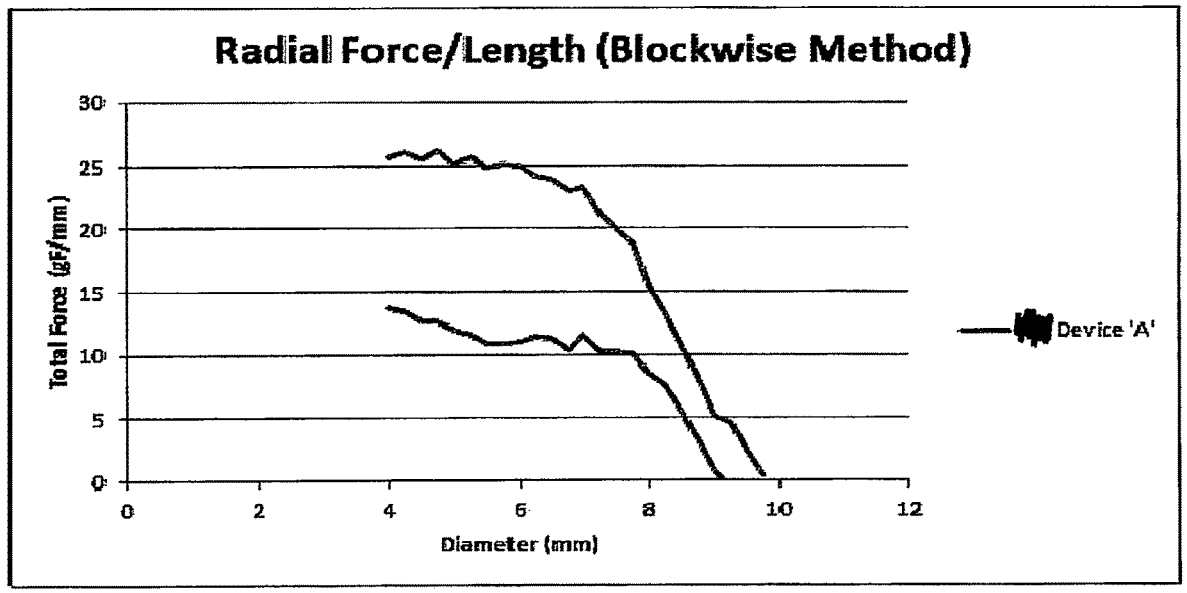
FIG. 9 shows radial force per unit length for the device of FIG. 8.

FIG. 8 shows total radial force versus corresponding vessel diameter for a device comprising the frame in accordance with embodiments. The total radial force comprises the force to the vessel wall along the length of the device FIG. 9 shows radial force per unit length for the device of FIG. 8. The radial force per unit length comprises the amount of force to the vessel wall per unit length along the wall, for example in millimeters.

Figure 10:
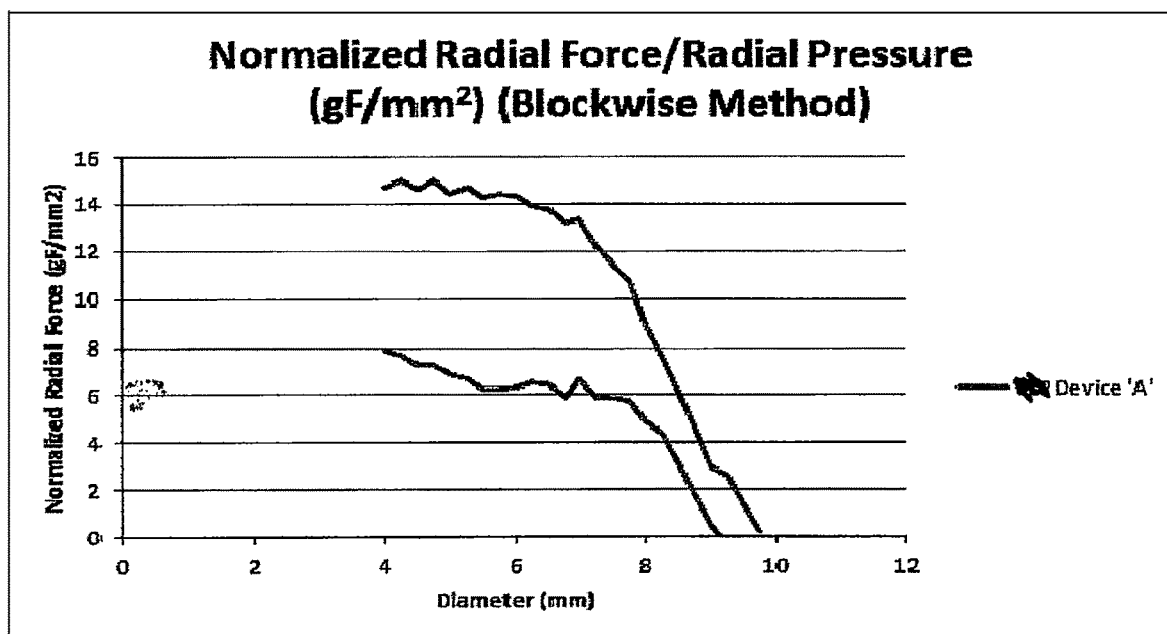
FIG. 10 shows normalized radial force for the device of FIGS. 8 and 9 in accordance with embodiments.

FIG. 10 shows normalized radial force for the device of FIGS. 8 and 9 in accordance with embodiments. The normalized radial force comprises the amount of force per unit contact area of the device on the vessel wall, for example in gF/mm2.

TABLE 2

Estimation for Total Force (gF) UTL-LTL

| Vessel | Blockwise Method | | Belt Loop Method | |
|---|---|---|---|---|
| Range | UTL | LTL | UTL | LTL |
| Device A 5-7 mm | 2073 | 10.4 | 592.2 | 2.97 |
| Device B 6-9 mm | 2583 | 12.9 | 737.9 | 3.69 |
| Device C 8-12 mm | 2583 | 12.9 | 737.9 | 3.69 |

TABLE 3

Estimation for Force/Length (gF/mm) UTL-LTL

| Vessel | Blockwise Method | | Belt Loop Method | |
|---|---|---|---|---|
| Range | UTL | LTL | UTL | LTL |
| Device A 5-7 mm | 121.9 | 0.6097 | 34.84 | 0.1742 |
| Device B 6-9 mm | 133.8 | 0.6691 | 38.23 | 0.1912 |
| Device C 8-12 mm | 144.7 | 0.7235 | 41.34 | 0.2067 |

The values in Tables 2 and 3 were determined based on the original 20 gF/mm2 and 0.1 gF/mm2 as described herein for the belt loop testing. A person of ordinary skill in the art can converted to equivalent total force and per unit length based on the device surface areas and lengths.

The metal to artery ratio as described herein can depend on the size of the arterial wall and can range from about 5% to about 10%, for example. For device A corresponding to vessel wall diameter A of 5 mm, the metal to artery ratio can be about 10%, and for device C corresponding to a vessel wall diameter 12 mm, the metal to artery ration can be about 5%, for example.

The embodiments as described herein are particularly well suited for treating patients having a wide range of anatomy at the target site such as the carotid sinus. In many embodiments, the transverse dimension of the device is configured to change in response systole and diastole in order to enhance stretching and stimulation of the baroreceptors. The connecting members of the frame can be configured to resiliently deflect in response to systole and diastole, such that transverse dimensions of the frame cycle back and forth between a first smaller transverse dimension during diastole and a second larger transverse dimension during systole.

In many embodiments, a transverse dimension across the frame increases by at least about 1% (one percent) in response to systole, and the amplitude of this cyclical variation in the cross-sectional dimension in response to systole and diastole can be within a range from about 0.5% to 10%, for example within a range from about 1% to 7%, from about 1.5% to 7%, from about 2% to 4%. In specific embodiments, the transverse distance across a cross-section of the frame increases by an amount within a range from about 2% to 3% from diastole to systole and decreases by a similar amount from systole to diastole. While the transverse dimension across the frame can be measured in many ways, in many embodiments the transverse dimension comprises a maximum distance between corner structures.

The plurality of neighboring longitudinal struts and the plurality of connecting members can be configured to provide a radial force to the vessel wall providing the percent changes in the transverse dimension across the frame. The plurality of neighboring longitudinal struts and the plurality of connecting members are configured to provide a radial force to the vessel wall within a range from about 0.1 gF (grams force) per mm (millimeter) to about 50 gF per mm (millimeter) in order to reshape the vessel wall. The radial force can be provided in terms of radial force per millimeter along the longitudinal direction of the vessel wall, for example.

In many embodiments, each of the corner structures comprising the plurality of neighboring longitudinal struts joined with transverse members comprises a substantially fixed configuration when the distance between the corner structures changes with deflection of the connecting members in response to systole and diastole, in order to provide the change in dimension across the frame.

The frame may comprise one or more of many known implantable biocompatible materials suitable for providing the dimensions and structures of the frame as described herein, and a person of ordinary skill in the art can construct the implantable frames in accordance with embodiments disclosed herein. For example, a person of ordinary skill in the art of stent design will be familiar materials and manufacturing processes suitable for constructing the implantable frame as disclosed herein. For example, the material of the frame may comprise a known stent alloy such as nitinol (Nickel Titanium alloy), for example.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. An implantable frame to form a wall of an artery, the implantable frame comprising:
   between three to five corner structures, each corner structure comprising (i) between two to three transverse members and (ii) two circumferentially adjacent longitudinal struts joined with the between two to three transverse members so as to define between one to two openings extending between the two circumferentially adjacent longitudinal struts of each corner structure; and
   between six to ten connecting members, each connecting member extending laterally between longitudinal ends of two circumferentially adjacent corner structures, the connecting members in combination with the circumferentially adjacent corner structures defining between three to five windows of the implantable frame, each window being sized to enhance pulsatility of the wall, each window defines a side of the frame and wherein each side of the frame comprises a single window
   wherein the implantable frame, when in an expanded profile configuration, defines a polygonal cross-section from a proximal end thereof to a distal end thereof, wherein the corner structures and the connecting members are arranged together to define the shape of the polygonal cross-section and the polygonal cross-section lies in a plane transverse to a longitudinal axis of the implantable frame, wherein the polygonal cross-section of the implantable frame changes a shape of the artery when the implantable frame is implanted therein, and wherein the polygonal cross-section has from three to five sides.

2. An implantable frame as in claim 1, wherein the between one and two openings of an individual corner structure, a thickness of the two circumferentially adjacent longitudinal struts of said individual corner structure, and a thickness of the between two and three transverse members of said individual corner structure are dimensioned to allow an endothelium of the vessel wall to grow over said individual corner structure.

3. An implantable frame as in claim 1, wherein, for each corner structure, the between one to two openings comprise between one to two slots extending in a longitudinal direction defined with the two circumferentially adjacent longitudinal struts of the corner structure and the between two to three transverse members that join said two circumferentially adjacent longitudinal struts.

4. An implantable frame as in claim 3, wherein the between one to two slots comprise between one to two longitudinal slots extending in a longitudinal direction between the two circumferentially adjacent longitudinal struts, the longitudinal slots defined with between two to three transverse members.

5. An implantable frame as in claim 1, wherein the implantable frame comprising a narrow profile configuration for delivery and an expanded profile configuration when deployed in order to decrease blood pressure and wherein the between three to five corner structures comprise a substantially fixed configuration and the between six to ten connecting members deflect when the implantable frame transitions from the narrow profile configuration to the expanded profile configuration.

6. An implantable frame as in claim 1, wherein the between three to five corner structures provide a decreased profile with deflection of the transverse members when delivered.

7. An implantable frame as in claim 1, wherein the pulsatility enhancing windows are shaped to receive at least a portion of the vessel wall within the window during diastole and to allow at least the portion of the vessel wall to move outside the window during systole in order to increase pulsatility and decrease blood pressure.

8. An implantable frame as in claim 7, wherein the longitudinal struts of the between three to five corner structures comprise a thickness extending in a radial direction away from the longitudinal axis of the implantable frame and wherein each of the pulsatility enhancing windows is dimensioned to allow at least the portion of the vessel wall to move a distance greater than the thickness between systole and diastole in order to increase pulsatility and decrease blood pressure.

9. An implantable frame as in claim 1, wherein the between three to five corner structures and the between six to ten connecting members are configured to provide a radial force to the vessel wall within a range from about 0.1 gF (grams force) per mm (millimeter) to about 50 gF per mm (millimeter) in order to reshape the vessel wall.

10. An implantable frame as in claim 1, wherein the between three to five corner structures and the between six to ten connecting members are configured to provide a radial contact pressure to the vessel wall within a range from about 0.5 gF (grams force) per mm2 (millimeter squared) to about 15 gF per mm2 (millimeter squared) in order to reshape the vessel wall.

11. An implantable frame as in claim 1, wherein the between three to five corner structures and the between six to ten connecting members are configured to provide a maximum total radial contact pressure to the vessel wall of about 15 gF per mm2 (millimeter squared) in order to reshape the vessel wall.

12. An implantable frame as in claim 1, wherein the between three to five corner structures, including the two longitudinal struts for each corner structure, and the between six to ten connecting members remain substantially fixed during systole and diastole in order to define between three to five substantially fixed windows and wherein the at least the portion of the vessel wall moves in relation to the substantially fixed windows.

13. An implantable frame as in claim 1, wherein the between six to ten connecting members deflect at least partially during systole and diastole to change a cross-sectional size of the frame and a size of the plurality of windows.

14. An implantable frame as in claim 1, wherein each connecting members extends at an angle from each of a pair of circumferentially adjacent corner structures, the angle corresponding to an angle of the corner of the polygonal cross-section.

15. An implantable frame as in claim 1, wherein the implantable frame comprises a single window in the longitudinal direction along a side of the frame.

16. An implantable frame as in claim 1, wherein a longitudinal window length comprises at least about sixty per cent of an overall longitudinal length of the frame when the frame comprises an expanded deployed configuration.

17. An implantable frame as in claim 1, wherein the implantable frame is configured to modulate baroreceptor activity and wherein the device is configured to treat hypertension and increase one or more of heart function or renal function and wherein the device is configured to decrease a likelihood of stroke.

18. An implantable frame as in claim 1, wherein, for each of the corner structures, two of the transverse members connect to the two circumferentially adjacent longitudinal struts on the longitudinal ends of said struts in order to inhibit separation and deflection of the circumferentially adjacent longitudinal struts.

19. An implantable frame as in claim 1, wherein the connecting members are configured to deflect in response to systole and diastole in order to change a cross-sectional dimension between a plurality of corner structures, and wherein the cross-sectional dimension changes within a range from about 0.5% to 10%.

20. An implantable frame as in claim 19, wherein, for each of the corner structures, the transverse members connect to the two circumferentially adjacent longitudinal struts on the longitudinal ends of the struts in order to inhibit separation and deflection of the two circumferentially adjacent longitudinal struts when the connecting members deflect and change the cross-sectional dimension between the corner structures in response to systole and diastole.

21. An implantable frame as in claim 1, wherein the polygonal cross-section has four sides.

22. An implantable frame as in claim 1, wherein, for each of the corner structures, the two circumferentially adjacent longitudinal struts are substantially parallel to the longitudinal axis of the implantable frame.

23. An implantable frame as in claim 1, wherein each window of the implantable frame is circumferentially adjacent a first opening of a first corner structure on a first lateral side of said window and circumferentially adjacent a second opening of a second corner structure on a second lateral side of said window opposite the first lateral side.

24. An implantable frame as in claim 1, wherein each opening of the corner structures of the implantable frame is circumferentially adjacent a first window on a first lateral side of said opening and circumferentially adjacent a second window on a second lateral side of said opening opposite the first lateral side.

25. An implantable frame as in claim 1, wherein the plurality of openings of the corner structures and the plurality of windows alternate with each other in a circumferential direction of a transverse plane of the implantable frame.

26. An implantable frame as in claim 1, wherein each connecting member comprises a first extension, a second extension, and an intermediate portion connecting the first and second extensions, wherein the first extension extends at a first angle from a longitudinal end of a first longitudinal strut of a first corner structure, and wherein the second extension extends at a second angle from a longitudinal end of a second longitudinal strut of a second corner structure circumferentially adjacent the first corner structure.

\* \* \* \* \*